US005129397A

United States Patent [19]
Jingu et al.

[11] Patent Number: 5,129,397
[45] Date of Patent: Jul. 14, 1992

[54] ULTRASONIC DIAGNOSING APPARAUTS

[75] Inventors: Masaharu Jingu; Tomohiro Sato; Miwako Aida, all of Ootawara, Japan

[73] Assignee: Kabushiki Kaisha Toshiba, Kawasaki, Japan

[21] Appl. No.: 572,244

[22] Filed: Aug. 27, 1990

[30] Foreign Application Priority Data
Aug. 30, 1989 [JP] Japan .................................. 1-223704

[51] Int. Cl.$^5$ .............................................. A61B 8/00
[52] U.S. Cl. ................... 128/660.01; 248/581
[58] Field of Search ............... 128/660.01, 660.07; 248/580–581, 585, 648, 660–667, 676–678

[56] References Cited

U.S. PATENT DOCUMENTS

| | | | |
|---|---|---|---|
| 4,625,731 | 12/1986 | Quedens et al. | 128/660.07 |
| 4,870,954 | 10/1989 | Satoh | 128/660.07 X |

FOREIGN PATENT DOCUMENTS

| | | | |
|---|---|---|---|
| 3821074 | 1/1989 | Fed. Rep. of Germany | 128/660.07 |

OTHER PUBLICATIONS

Soldner, R. et al "The Vidoson 735—A New Real-Time Scanner for Ultrasonography", Electromedica 3-477, Germany pp. 107–112.

Primary Examiner—Francis Jaworski
Attorney, Agent, or Firm—Oblon, Spivak, McClelland, Maier & Neustadt

[57] ABSTRACT

An ultrasonic diagnosing apparatus includes a main body, an ultrasonic probe with a a cable, an expansive support portion, a horizontal arm, a table, and a lever, and a display unit. One end of the support portion is attached to the main body. One end of the horizontal arm is attached to the other end of the support portion. The horizontal arm includes a rotating mechanism for horizontally rotating about the support portion and a mechanism for locking and unlocking the rotating mechanism. A portion of the table is attached to the other end of the horizontal arm. The table includes a pivot mechanism for horizontally pivoting about the horizontal arm and a mechanism for locking and unlocking the pivot mechanism. The lever is arranged on the table so as to bias the locking and unlocking mechanism. The display unit is arranged on the table through a mechanism for allowing it to be tilted.

17 Claims, 14 Drawing Sheets

FIG. 14C

ULTRASONIC DIAGNOSING APPARAUTS

BACKGROUND OF THE INVENTION

1. Field of the Invention

The present invention relates to an ultrasonic diagnosing apparatus for obtaining ultrasonic data such as an M-mode display image (motion image), a B-mode display image (Tomography), a D-mode display image (blood flow speed image), and a DF-mode display image (CFM image: Color Flow Mapping image), and displaying a corresponding image for diagnosis.

2. Description of the Related Art

Figure 1:
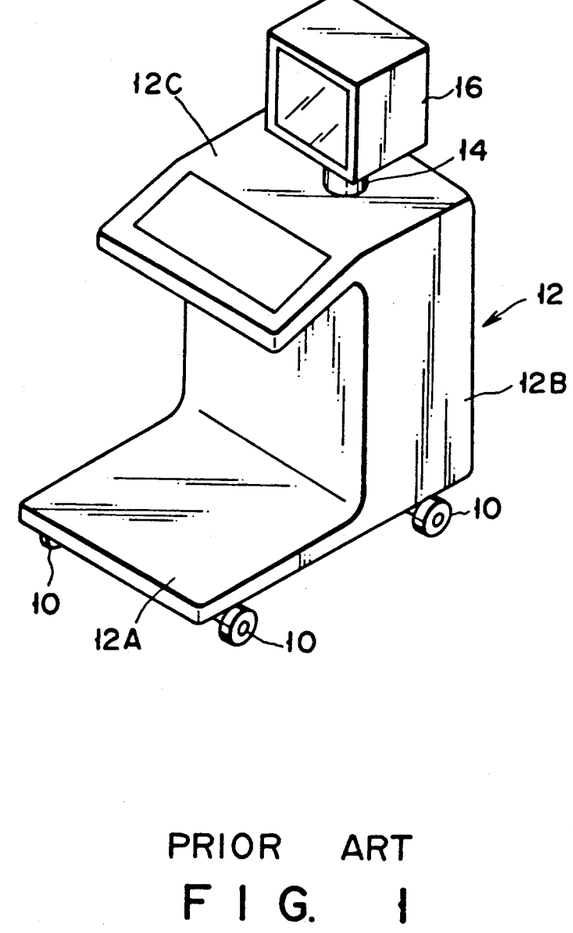
FIG. 1 is a schematic perspective view showing an arrangement of a conventional ultrasonic diagnosing apparatus.

FIG. 1 shows a conventional ultrasonic diagnosing apparatus of this type. Referring to FIG. 1, a substantially U-shaped main body 12 having casters 10 is constituted by a base portion 12A, an upright portion 12B, and a table 12C. A display unit 16 is arranged on the table 12C of the main body 12 through a support member 14. In this case, the upright portion 12B incorporates various electronic circuit boards. In addition, operating units such as a keyboard are incorporated in the table 12C. An ultrasonic probe (not shown) extends from the main body 12.

In the ultrasonic diagnosing apparatus having such an arrangement, diagnosis, e.g., an operation of the apparatus is performed in the following manner. An operator (not shown) such as a doctor carries the apparatus into a room where a subject to be examined (patient) is present. Alternately, the subject is brought to a consultation room where the apparatus is installed. In the former case, for example, the apparatus is placed beside a bed, and the power source of the apparatus is turned on to start the apparatus. In diagnosis, the probe is brought into contact with the subject so as to transmit/receive ultrasonic waves to/from a desired portion of the subject, and an image based on reflection echoes is observed through the display unit 16.

In such an ultrasonic diagnosing apparatus, sophisticated signal processing representing the functional characteristics of the apparatus or methods of obtaining high-quality images have been extensively studied and improved. However, other characteristics such as operability have not been satisfactorily studied yet.

A medical apparatus of this type tends to be placed within a small space. In addition, a doctor is to operate the apparatus in the small space, and must also perform operations such as diagnosis with respect to a subject to be examined. Therefore, especially high operability is required. In addition, a high space factor, i.e., high utilization efficiency of a space is required.

SUMMARY OF THE INVENTION

It is an object of the present invention to provide an ultrasonic diagnosing apparatus having high operability in diagnosis and a high space factor.

In order to achieve the above object, according to the present invention, there is provided an ultrasonic diagnosing apparatus comprising:

a main body placed on a floor and incorporating electrical elements for performing ultrasonic transmission/reception, signal processing, and power supply;

an ultrasonic probe with a cable, extending from the main body, for transmitting/receiving ultrasonic transmission/reception signals;

a support portion having one end portion attached to the main body;

an operating table, having one end portion attached to the other end of the support portion so as to be translated, for performing an operation for ultrasonic diagnosis; and a display portion, arranged on the operating table, for displaying data generated by the signal processing in the main body.

In order to achieve the above object, according to the present invention, there is also provided an ultrasonic diagnosing apparatus comprising:

a main body having casters arranged on a lower portion of a casing thereof, the casing incorporating electrical elements for performing ultrasonic transmission, signal processing, and power supply;

an ultrasonic probe with a cable, extending from the main body, for transmitting/receiving ultrasonic transmission/reception signals;

an extendible support portion having one end portion attached to the main body;

a horizontal arm having one end portion attached to the other end of the support portion, the horizontal arm including a rotating mechanism for horizontally rotating about the support portion and a mechanism for locking and unlocking the rotating mechanism;

a table having a portion attached to the other end of the horizontal arm, the table including a pivot mechanism for horizontally pivoting about the horizontal arm and an mechanism for locking and unlocking the pivot mechanism;

a lever, arranged on the table, for biasing the locking and unlocking mechanism of the table; and a display unit arranged on the table through a mechanism for rotating and tilting operations.

In order to achieve the above object, according to the present invention, there is also provided an ultrasonic diagnosing apparatus comprising:

a main body placed on a floor and incorporating electrical elements for performing ultrasonic transmission/reception, signal processing, and power supply;

an ultrasonic probe with a cable, extending from the main body, for transmitting/receiving ultrasonic transmission/reception signals;

a support portion having one end portion attached to the main body so as to allow the support portion to be tilted;

an operating table having one end portion attached to the other end of the support portion so as to allow the operating table to be tilted; and a display portion, arranged on the operating table, for displaying data obtained by the signal processing in said main body.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

An ultrasonic diagnosing apparatus according to an embodiment of the present invention will be described below with reference to FIGS. 2 to 10.

Figure 4:
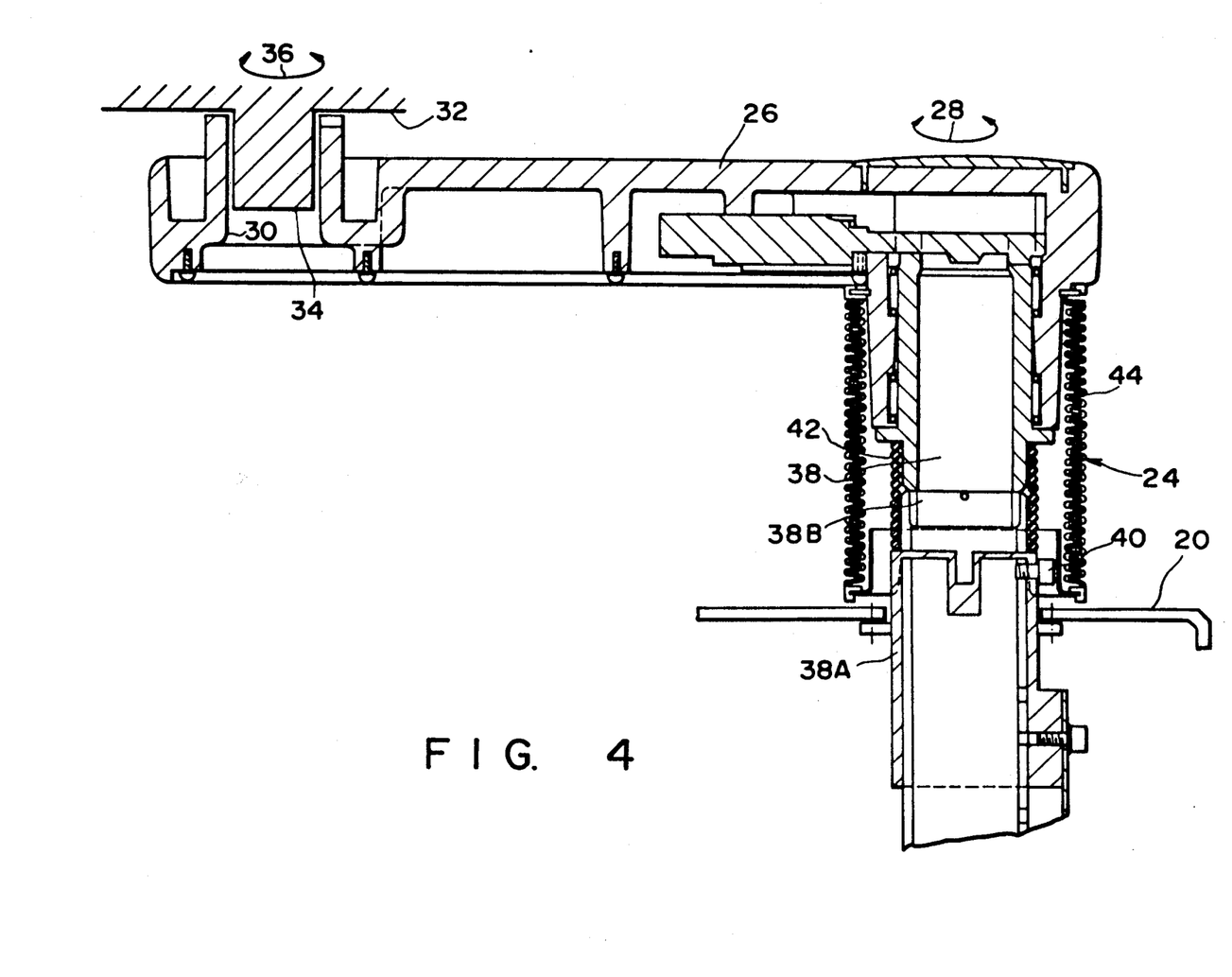
FIG. 4 is a view showing a mounting structure of a main body and a support portion in the ultrasonic diagnosing apparatus in FIG. 2.

Referring to FIGS. 2, 3A, 3B, 3C, 3D, and 4, the ultrasonic diagnosing apparatus of this embodiment includes a main body 20 incorporating an ultrasonic transmission/reception unit, a signal processor, a power source, and the like. Casters 22 are arranged at the four corners of the lower surface of the casing of the main body 20. One end portion of an expansive support portion 24 is fixed on a corner of the upper surface of the main body 20 at a right angle. FIG. 4 shows the support portion 24 in detail. One end portion of a horizontal arm plate 26 is axially supported by the other end portion of the support portion 24 so as to be horizontally rotatable. That is, a bearing (not shown) is formed in the other end portion of the horizontal arm plate 26 so as to allow the other end portion of the support portion 24 as a fixed shaft to be inserted. With this arrangement, the horizontal arm plate 26 can be rotated about the support portion 24 in a direction indicated by an arrow 28. In addition, a bearing hole 30 is formed in the other end portion of the horizontal arm plate 26, and a rod 34 (not shown) formed on the lower surface of a table 32 is inserted in the bearing hole 30 so that the table 32 can be rotated about the horizontal arm plate 26 in a direction indicated by an arrow 36.

The support portion 24 includes a double cylindrical member as a main constituent element. One end portion of an outer cylinder 38A is fixed to the main body 20 while one end portion of an inner cylinder 38B is inserted in the other end portion of the outer cylinder 38A. In addition, the other end portion of the inner cylinder 38B constitutes a portion for axially supporting the horizontal arm plate 26. The total length of the double cylindrical member 38 can be changed by pulling it in its longitudinal direction. That is, the support portion 24 has an extendible structure. The longitudinal length of the double cylindrical member 38 can be set by fixing the inner cylinder 38B by a screw 40 threadably inserted from the outer cylinder 38A. In addition, a coil spring 42 for supporting a load applied to the inner cylinder 38B is arranged in the double cylindrical member 38. A bellows portion 44 is formed on the outer surface of the double cylindrical member 38.

Figure 2:
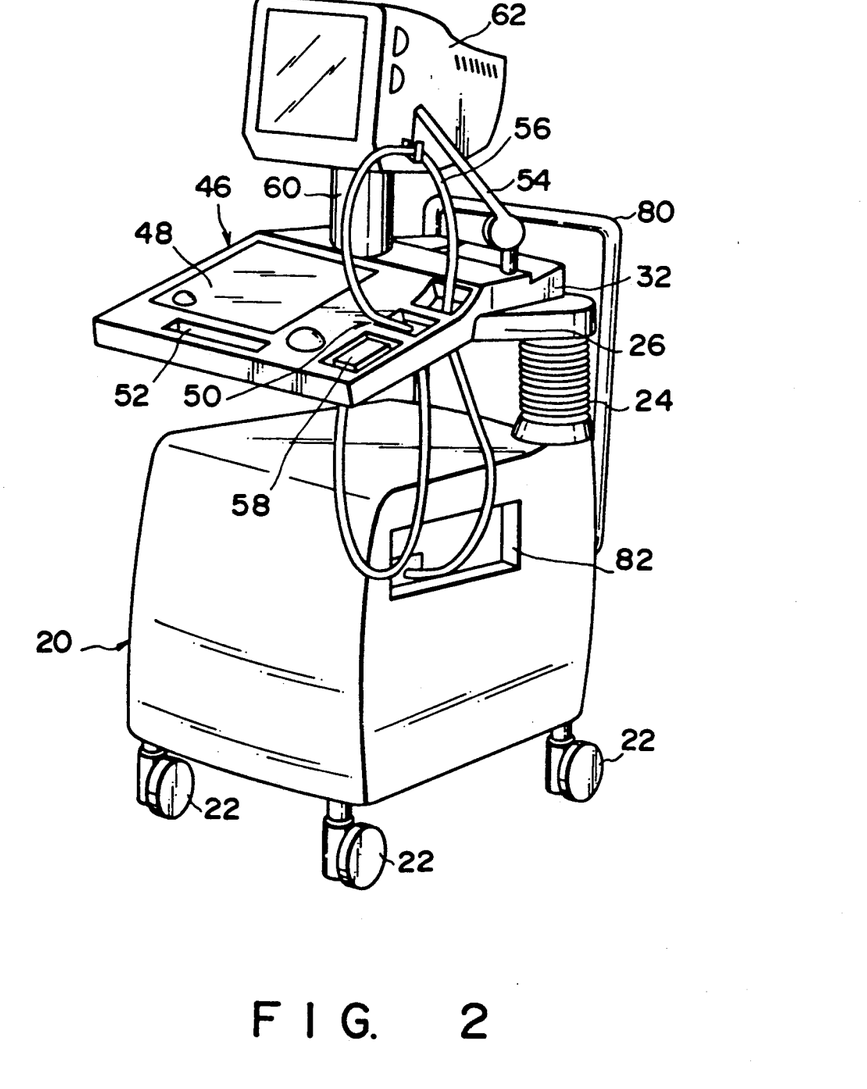
FIG. 2 is a perspective view showing an arrangement of an ultrasonic diagnosing apparatus according to an embodiment of the present invention.
Figure 3A:
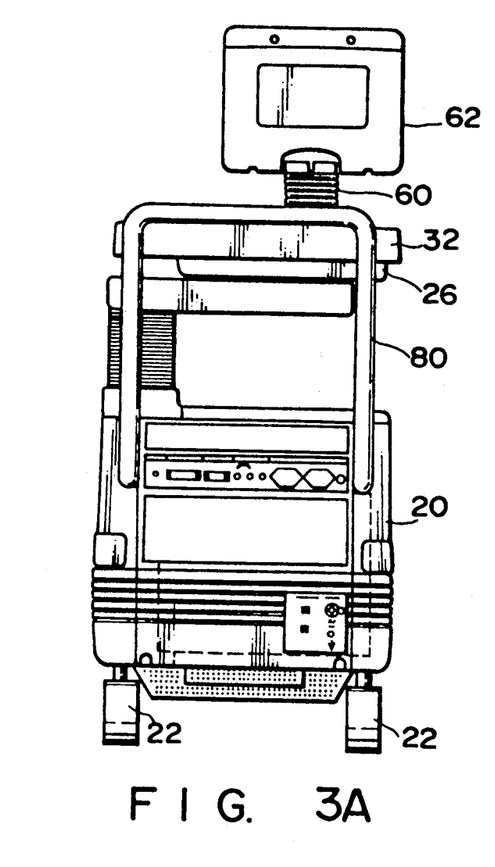
FIG. 3A is a rear view of the ultrasonic diagnosing apparatus in FIG. 2.
Figure 3B:
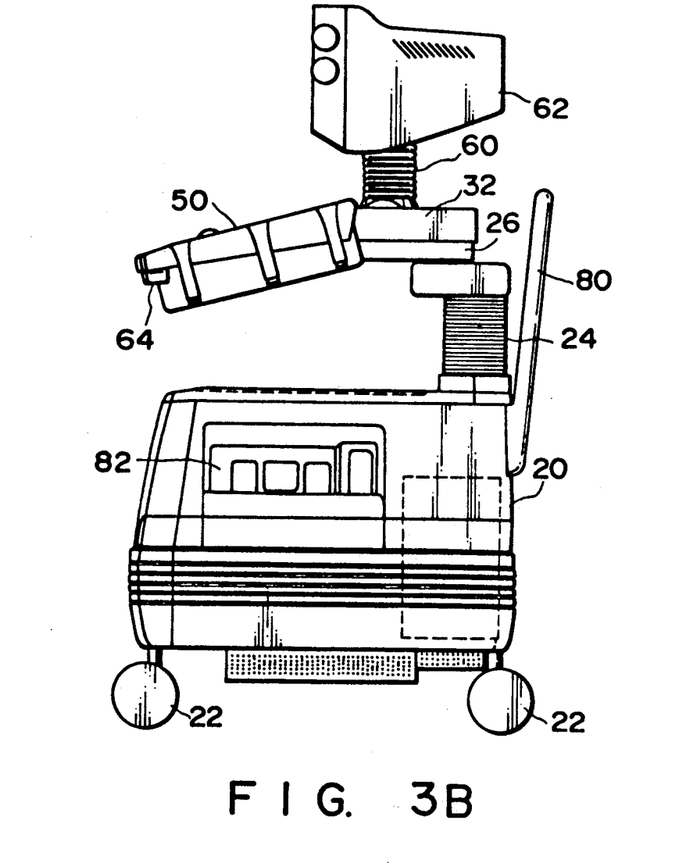
FIG. 3B is a right side view of the ultrasonic diagnosing apparatus in FIG. 2.
Figure 3C:
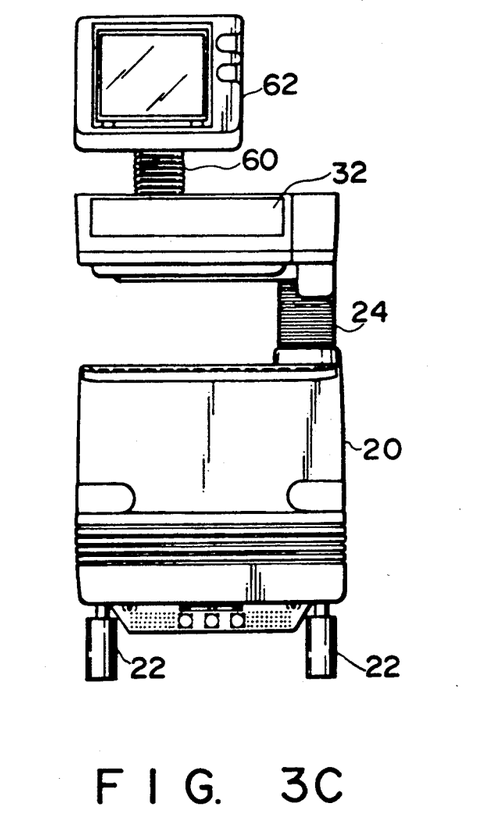
FIG. 3C is a front view of the ultrasonic diagnosing apparatus in FIG. 2.
Figure 3D:
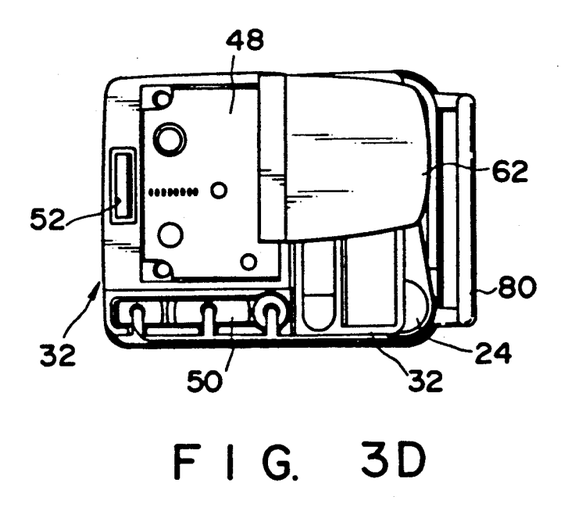
FIG. 3D is a top view of the ultrasonic diagnosing apparatus in FIG. 2.

As shown in FIG. 2, the table 32 serving as an operating table portion is constituted by a body portion 46, an operating portion 48 arranged on the body portion 46 and including various operating elements such as a keyboard, a cable rack portion 50, and a grip portion 52 obtained by forming an elongated hole in a front portion of the operation portion 48. The following components are arranged on the body portion 46: a cable hanger 54, a probe cable 56 suspended from the cable hanger 54, and a probe 58 attached to an end portion of the probe cable 56. In addition, a display 62 is arranged on the body portion 46 through a support member 60. A mechanism (not shown) for swinging and tilting operations is incorporated in an attaching portion of the support member 60 and the display 62.

Figure 5:
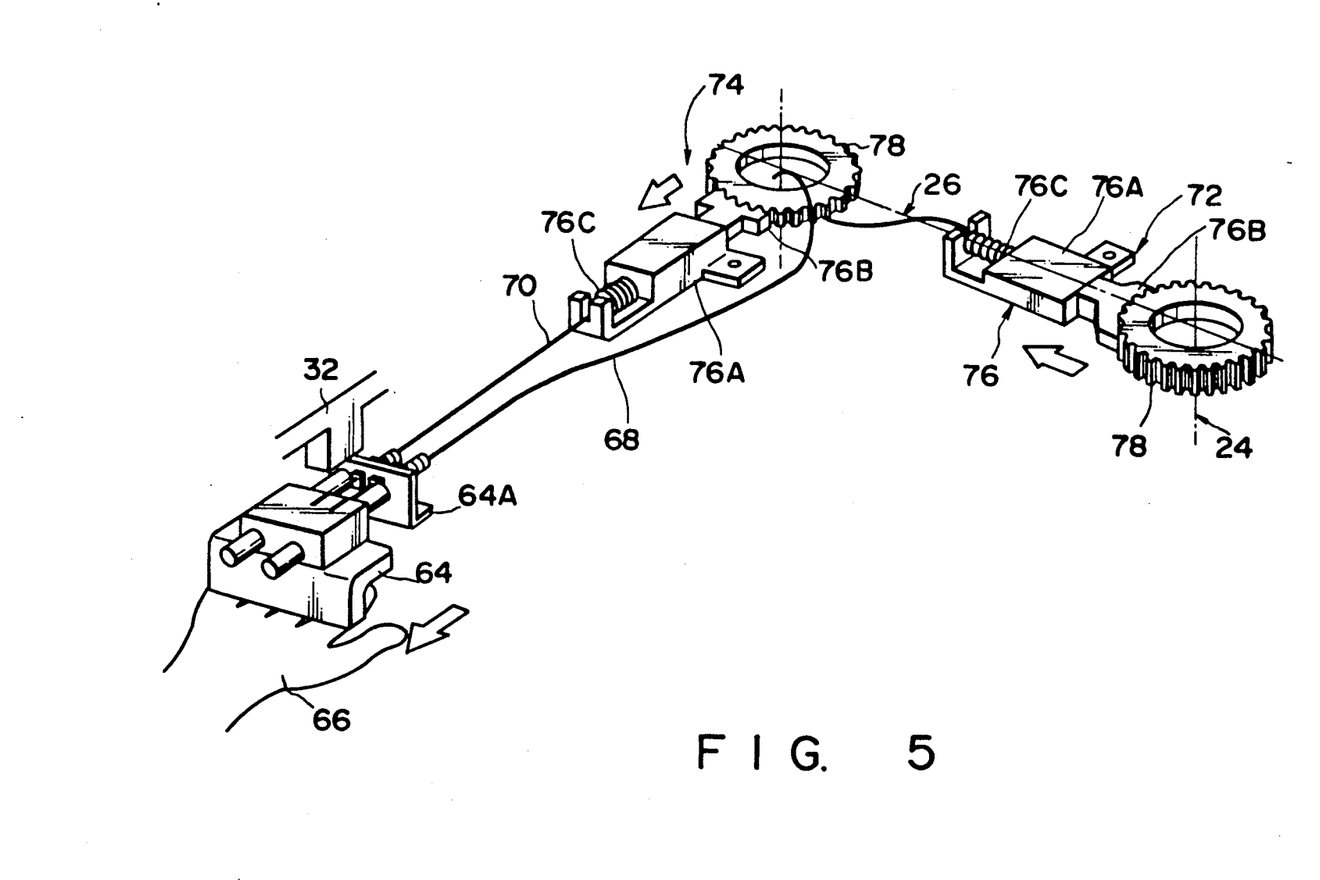
FIG. 5 is a schematic perspective view showing a main part of a lock mechanism arranged in the ultrasonic diagnosing apparatus in FIG. 2.

The horizontal arm plate 26 can be arbitrarily translated with respect to the support portion 24 and can be held in the resultant state. The body portion 46 can be arbitrarily translated with respect to the horizontal arm plate 26, and the resultant state can be held or canceled. FIG. 5 shows a schematic arrangement of a mechanism for translating these components and holding and canceling their states. More specifically, a lock piece 64A is fixed to the table 32, and a lever 64 is attached to the lock piece 64A. When the lever 66 is pulled by a hand 66 in a direction indicated by an arrow in FIG. 5, two wires connected to the lever 64 are pulled in the same direction. As a result, one wire 68 biases a first lock mechanism 72, and the other wire 70 biases a second lock mechanism 74. The first and second lock mechanism 72 and 74 have the same arrangement. The first lock mechanism 72 is arranged at a coupling portion between the upper portion of the support portion 24 and the horizontal arm 26. The second lock mechanism 74 is arranged at a coupling portion between the horizontal arm 26 and the table 32. An arrangement of the first lock mechanism 72 as a representative will be described below. The lock mechanism 72 is constituted by a lock bar 76 and a gear 78 locked by the lock bar 76. The lock bar 76 comprises a casing 76A, a lock piece, 76B, and a spring 76C. The lock piece 76B is slidably arranged in the casing 76A, and is moved by the wire 68 in a direction indicated by an arrow in FIG. 5 and the opposite direction. The lock piece 76B has a gear formed on its end portion which is meshed with the gear 78. The spring 76C is arranged in the casing 76A so as to bias the lock piece 76B in a direction indicated by an arrow in FIG. 5 and the opposite direction. With this arrangement, when the lever 64 is pulled by the hand 66 in the direction indicated by the arrow in FIG. 5, the two wires 68 and 70 connected to the lever 64 are pulled in the same direction. As a result, the lock piece 76B of each of the first and second lock mechanisms 72 and 74 is returned in the direction indicated by the arrow in FIG. 5, the gear of the lock piece 76B and the gear 78 are disengaged from each other. If the lever is restored to the previous position, the gear of the lock piece 76B and gear 78 are meshed with each other and locked.

Figure 6:
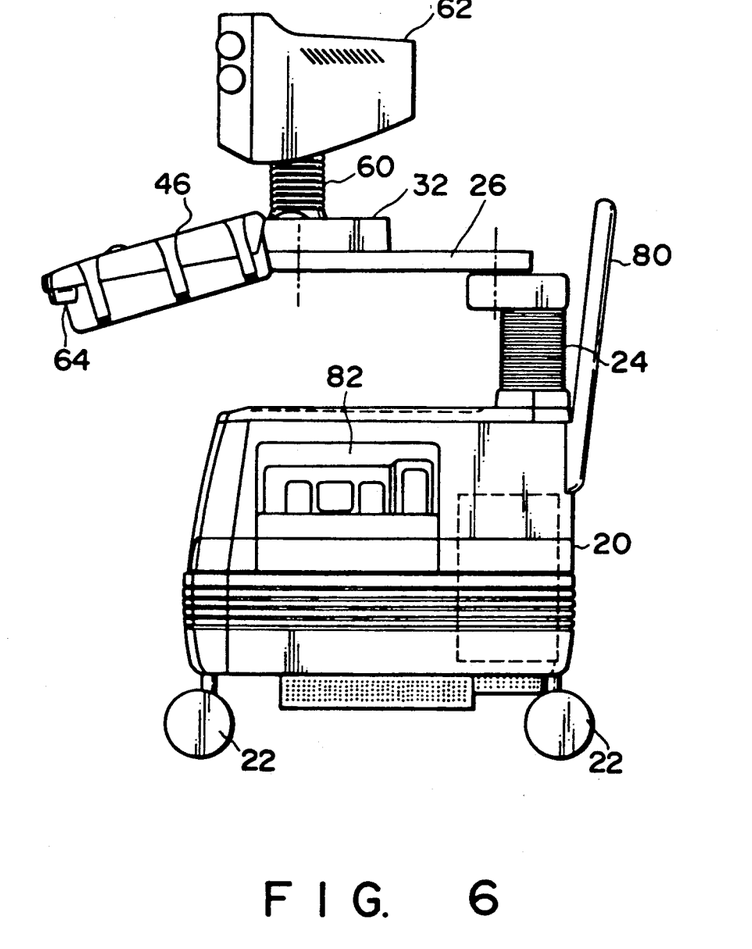
FIG. 6 is a right side view showing a state wherein a table of the ultrasonic diagnosing apparatus in FIG. 2 can be translated forward.
Figure 7:
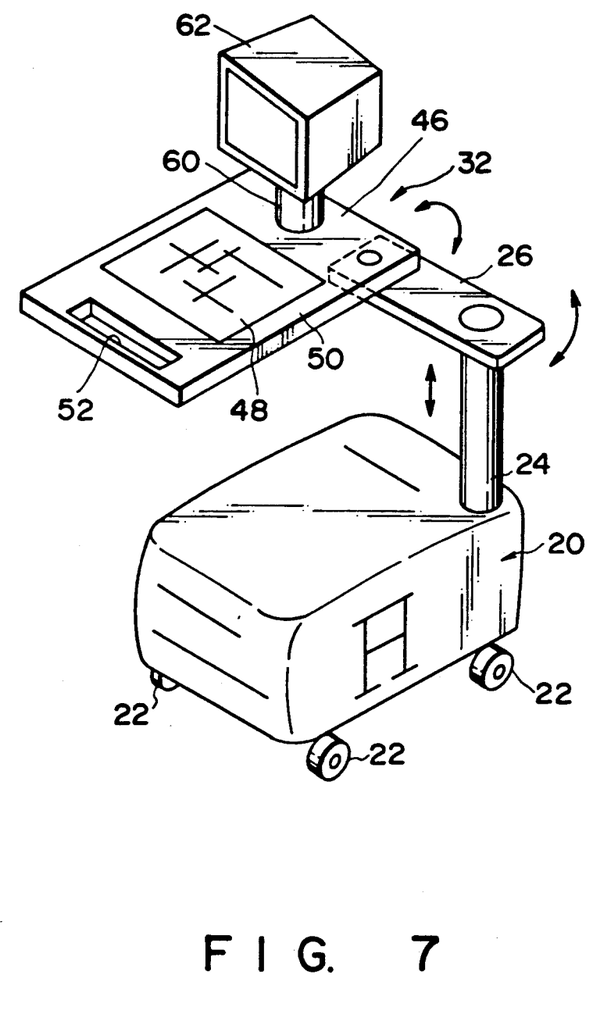
FIG. 7 is a schematic perspective view showing a state wherein the table of the ultrasonic diagnosing apparatus in FIG. 2 can be laterally translated.

The lock piece 64A is fixed to the table 32. The gear 78 of the first lock mechanism 72 is fixed to the upper portion of the support portion 24. The lock bar 76 of the first lock mechanism 72 is fixed to the horizontal arm plate 26. The lock bar 76 of the second lock mechanism 74 is fixed to the table 32. With this arrangement, when the lever 64 is pulled in the direction indicated by the arrow in FIG. 5, the locking states of the first and second lock mechanism 72 and 74 are canceled. As a result, the table 32 can be pulled to a desired position by holding the grip portion 52 as shown in FIG. 6, or can be translated to a desired position as shown in FIG. 7. If the lever 64 is moved in the direction opposite the direction indicated by the arrow in FIG. 5, the first and second lock mechanisms are locked again to perform positioning of the table 32.

Note that reference numeral 80 denotes a push-handle mounted on the rear portion of the main body 20; and 82, a connector box for the cable 56 and the like which is arranged in a side surface of the main body.

As described above, according to the apparatus of this embodiment, since the table 32 on which the operating portion 48 and the display 62 are arranged and the horizontal arm plate 26, and the horizontal arm 26 and the main body 20 can be relatively translated, an operator can operate the table 32 and the display 62 regardless of the position of the operation. With this increase in the degree of freedom of operation, the space factor can be improved.

Figure 8:
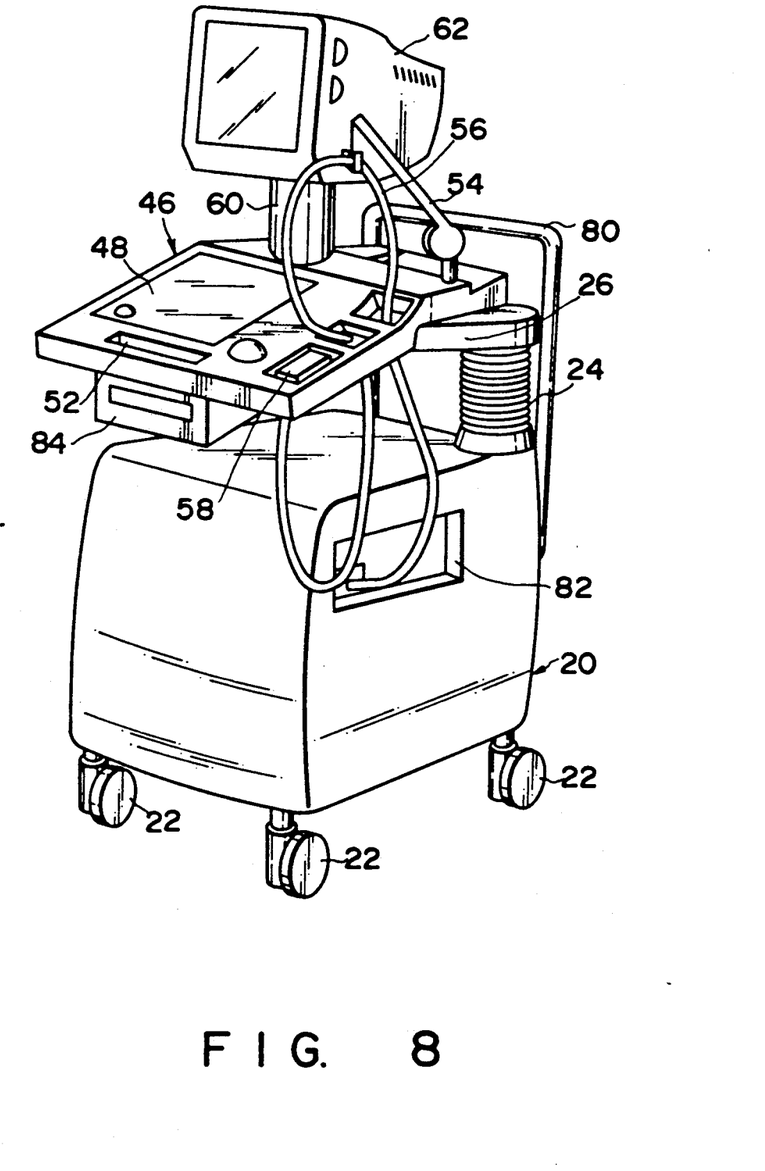
FIG. 8 is a perspective view showing a state wherein an accessory is mounted on the lower surface of the table of the ultrasonic diagnosing apparatus in FIG. 2.
Figure 9:
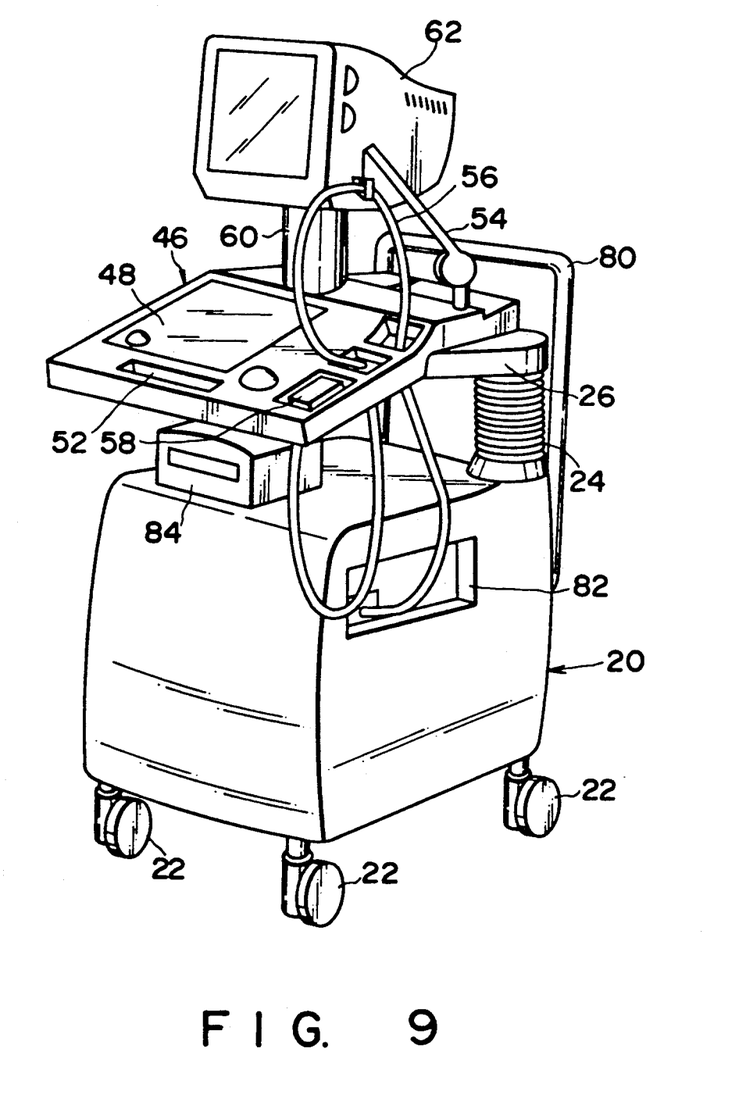
FIG. 9 is a perspective view showing a state wherein the accessory is mounted on the upper surface of the main body of the ultrasonic diagnosing apparatus in FIG. 2.

In addition, according to the apparatus of this embodiment, since the main body 20 and the table 32 are coupled to each other through the support portion 24, a space is formed between the main body 20 and the table 32. Accessories such as a video cassette recorder and an electrocardiograph, or a chair used by the operator can be placed in this space. This also improves the space factor. Various ways of using the above-mentioned space will be described below with reference to FIGS. 8 to 10. FIG. 8 shows a case wherein an accessory 84 is attached to the lower surface of the table 32. FIG. 9 shows a case wherein the accessory 84 is attached to the upper surface of the main body 20.

Figure 10:
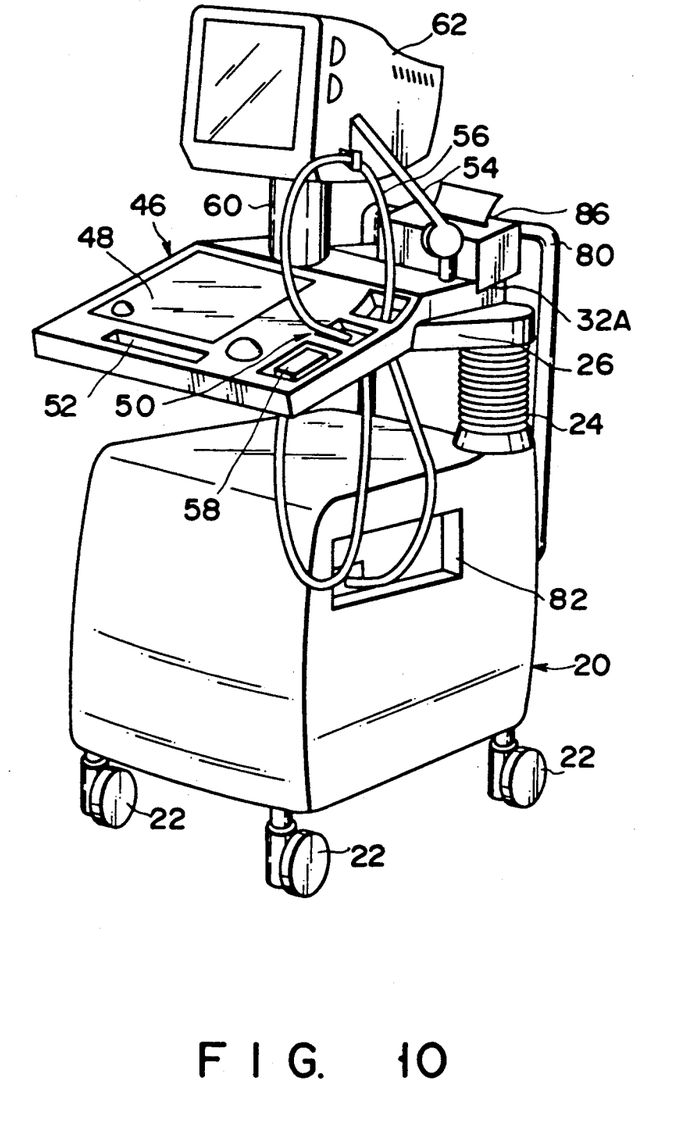
FIG. 10 is a perspective view showing a state wherein a tissue-paper box is mounted on the upper surface of the table of the ultrasonic diagnosing apparatus in FIG. 2.

FIG. 10 shows a case wherein a step 32A is formed in a rear portion of the table 32, and a tissue-paper box 86 is placed on the step 32A.

Figure 11:
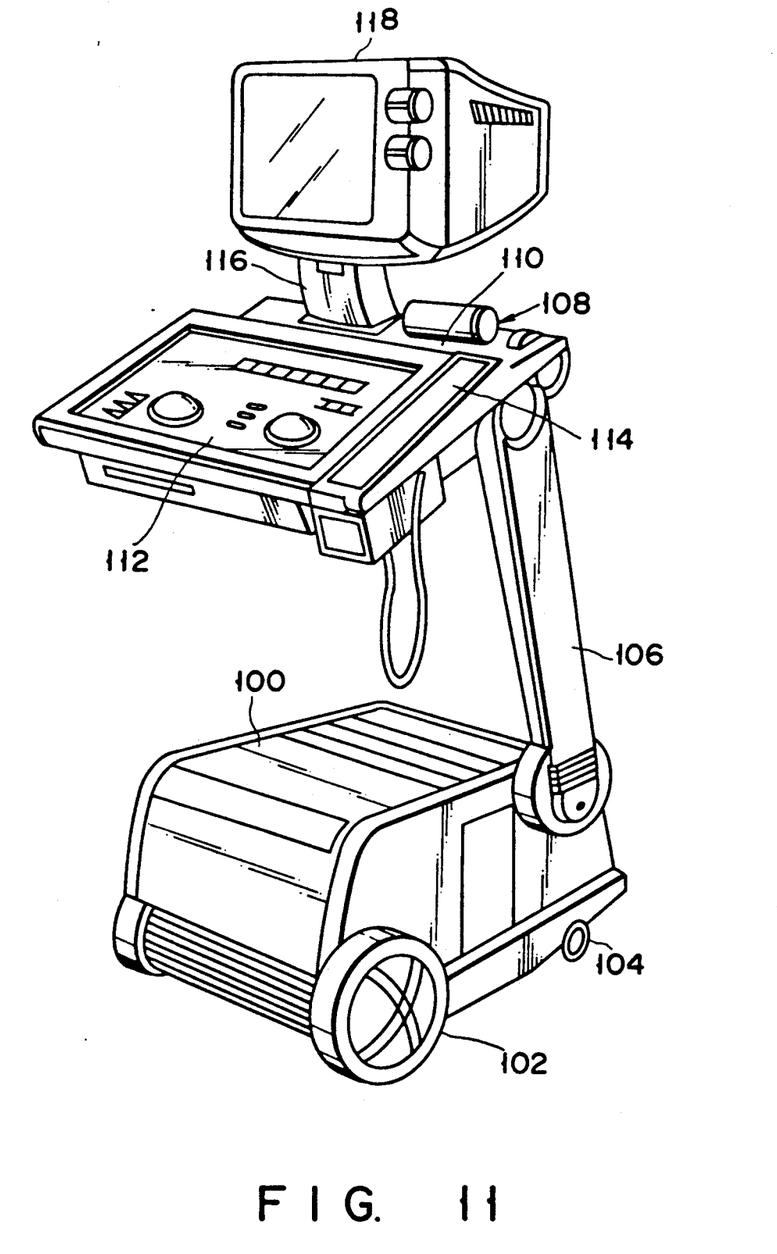
FIG. 11 is a perspective view showing an arrangement of an ultrasonic diagnosing apparatus according to another embodiment of the present invention.

An ultrasonic diagnosing apparatus according to another embodiment of the present invention will be described below with reference to FIG. 11. As shown in FIG. 11, the ultrasonic diagnosing apparatus includes a main body 100 incorporating an ultrasonic transmission/reception unit, a signal processor, a power source, and the like. Large casters 102 and small casters 104 are respectively arranged at the four corners on the lower surface of the casing of the main body 100.

One end portion of a support 106 is axially supported on one side wall of the main body 100. The other end portion of the support 100 is axially supported by one side wall of a table 108. The table 108 comprises a body portion 110, an operating portion 112 arranged on the body portion 110 and having various operation elements such as a keyboard, and a cable rack portion 114.

Figure 12:
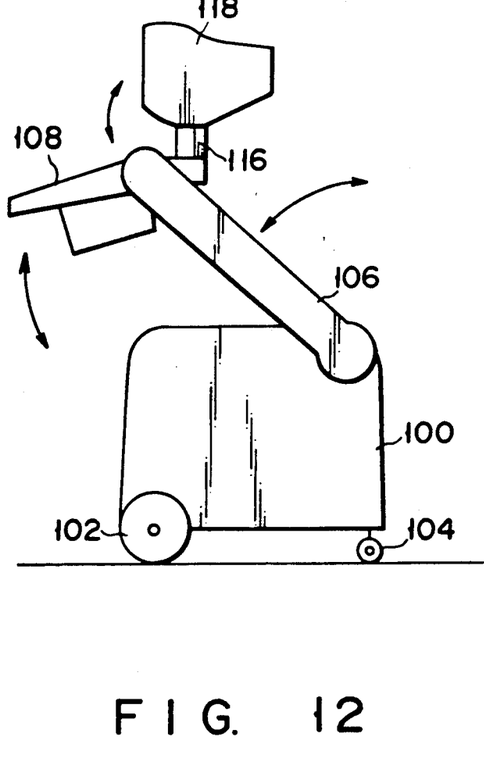
FIG. 12 is a schematic right side view showing a basic operation of the ultrasonic diagnosing apparatus in FIG. 11.

As shown in FIG. 12, the support 106 for axially supporting the main body 100 and the table 108 is designed to arbitrarily tilt the main body 100 and the table 108 and to hold the resultant states.

Figure 13:
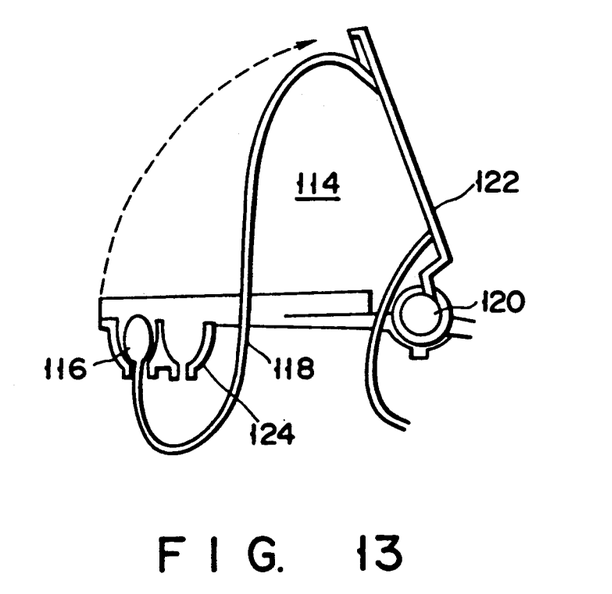
FIG. 13 is a side view showing an operation of a cable box of the ultrasonic diagnosing apparatus in FIG. 11.

As shown in FIG. 13, the cable rack portion 114 serves to hold an ultrasonic probe 116 and a cable 118, and is constituted by a shaft 120, a rack 122 axially supported by the shaft 120 so as to be freely rotated through 360°, and a probe holder 124. While the probe 116 is not used, the rack 122 is closed on the body portion 110 side. When the probe 116 is to be used, the rack 122 is raised from the body portion 110 side to be opened. A display 118 is mounted on the body portion 110 through a support member 116. This display 118 can be swung and tilted.

An operation of this embodiment having the above-described structure will be described below. According to this embodiment, since the table 108, the display 118, and the main body 100 can be relatively tilted by the support 106, the table 108 and the display 118 can be operated regardless of the position of an operator 128, e.g., in a standing position or a sitting position. With this increase in degree of freedom in operation, the space factor can be improved.

Figure 14A:
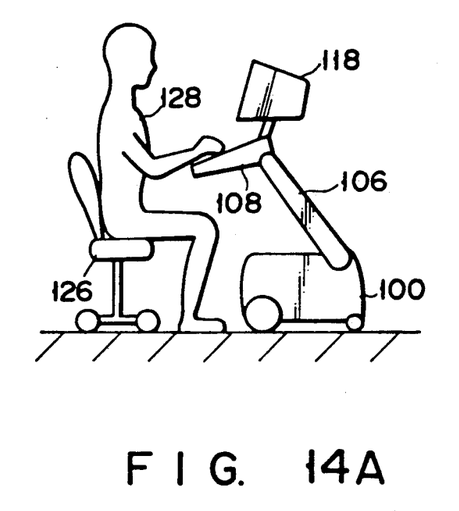
FIG. 14A is a schematic side view showing a state wherein the ultrasonic diagnosing apparatus in FIG. 11 can be operated by a doctor while he/she is sitting.
Figure 14B:
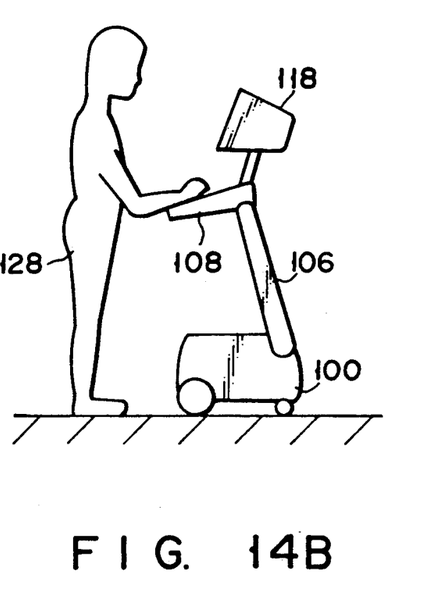
FIG. 14B is a schematic side view showing a state wherein the doctor can operate the ultrasonic diagnosing apparatus in FIG. 11 while he/she is standing.
Figure 14C:
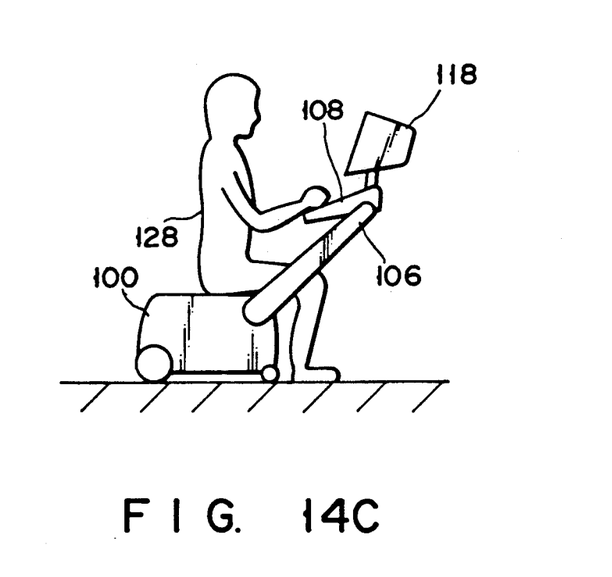
FIG. 14C is a schematic side view showing a state wherein the ultrasonic diagnosing apparatus in FIG. 11 can be operated by the doctor while he/she is sitting on a main body.

For example, FIGS. 14A to 14C show ways of operating the apparatus shown in FIG. 11. As shown in FIG. 14A, a chair 124 is placed beside the main body 100, and the table 108 and the display 118 can be operated while the operator 128 is sitting on the chair 126.

In addition, as shown in FIG. 14B, the operating portion 112 can be operated while the operator 128 is standing beside the main body 100.

Moreover, as shown in FIG. 14C, the main body 100 can be used as a chair, and the table 108 and the display 118 can be operated while the operator 128 is sitting on the main body 100.

As has been described above, according to the present invention, the main body and the table including the operating portion and the display can be relatively translated by the support. With this increase in degree of freedom in operation, the space factor can be improved.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic diagnosing apparatus comprising:
   a main body having casters arranged at the four corners of the lower surface of a casing of the main body, and incorporating electrical elements for performing ultrasonic transmission/reception, signal processing, and power supply;
   an ultrasonic probe with a cable, extending from said main body, for transmitting/receiving ultrasonic transmission/reception signals;
   a support portion having one end portion attached to said main body;
   an operating table, having one end portion attached to the other end of said support portion so as to be translated, for performing an operation ultrasonic diagnosis, said operating table including an arm plate and a table, said arm plate having one end portion attached to the other end of said support portion and having a rotating mechanism for horizontally rotating about said support portion, and said table having a portion attached to the other end of said arm plate and having a pivot mechanism for horizontally pivoting about said arm plate;
   a display for displaying an ultrasonic data generated by said signal processing in said main body; and
   a support member placed on said table for supporting said display.

2. An apparatus according to claim 1, wherein said main body includes a push handle.

3. An apparatus according to claim 1, wherein said support portion includes an extendible mechanism, said extendible mechanism comprising an outer cylinder fixed to said arm plate, an inner cylinder having one end portion fixed to the main body and the other end portion inserted to the outer cylinder, and a coil spring for supporting a load applied to the inner cylinder.

4. An apparatus according to claim 1, wherein said horizontal arm includes a mechanism for locking and unlocking said rotating mechanism.

5. An apparatus according to claim 4, wherein said mechanism for locking and unlocking said rotating mechanism comprises at least one cable fixedly attached at one end to a lever means which can be pulled by an operator, and attached at a second end to a lock piece for causing one of engagement and disengagement with a gear member.

6. An apparatus according to claim 1, wherein said table includes a mechanism for locking and unlocking said pivot mechanism.

7. An apparatus according to claim 6, wherein said mechanism for locking and unlocking said pivot mechanism comprises at least one cable fixedly attached at one end to a lever means which can be pulled by an operator, and attached at a second end to a lock piece for causing one of engagement and disengagement with a gear member.

8. An apparatus according to claim 1, wherein said table includes a body portion having an operating portion mainly constituted by a keyboard, a grip portion, and display means.

9. An apparatus according to claim 1, wherein said table includes a first support body supporting an accessory so as to be placed on an upper portion of said main body.

10. An apparatus according to claim 1, wherein said table includes a second support body for supporting an accessory so as to be placed on an upper portion of said main body.

11. An apparatus according to claim 1, wherein said operating table includes a step portion for supporting a tissue-paper box.

12. An apparatus according to claim 1, wherein said table includes a step for supporting a tissue-paper box.

13. An apparatus according to claim 1, wherein said support member includes a rotating means for rotating said display and a tilting means for tilting said display.

14. An apparatus according to claim 1, wherein said support portion comprises a double cylindrical member having an outer cylinder fixed to said main body and an inner cylinder which can be pulled in a longitudinal direction so as to extend said support portion in a first direction or retract said support portion in a direction opposite to said first direction.

15. An ultrasonic diagnosing apparatus comprising:
   a main body having casters arranged on a lower portion of a casing thereof, said casing incorporating electrical elements for performing ultrasonic transmission, signal processing, and power supply;
   an ultrasonic probe with a cable, extending from said main body, for transmitting/receiving ultrasonic transmission/reception signals;
   an extendible support portion having one end portion attached to a corner of said main body, said extendible support portion sliding vertically;
   an arm plate having one end portion attached to the other end of said support portion, said arm plate including a rotating mechanism for horizontally rotating about said support portion and a mechanism for locking and unlocking said rotating mechanism;
   a table having a portion attached to the other end of said arm plate, said table having an operating portion mainly constituted by a keyboard, a grip portion, and a mechanism horizontally pivoted about said arm plate and a mechanism for locking and unlocking said pivot mechanism;
   a lever placed on the undersurface of said table so as to be operated by an operator, for biasing said locking and unlocking mechanism of said table;
   a display for displaying an ultrasonic data generated by said signal processing in said main body; and
   a support member placed on said table, for supporting said display and rotating and tilting said display.

16. An ultrasonic diagnosing apparatus comprising:
   a main body having casters arranged at the four corners of a lower surface of a casing of the main body and incorporating electrical elements for performing ultrasonic transmission/reception, signal processing, and power supply;
   an ultrasonic probe with a caster, extending from said main body, for transmitting/receiving ultrasonic transmission/reception signals;
   a support portion having one end portion attached to said main body so as to allow said support portion to be tilted;
   an operating table having one end portion attached to the other end of said support portion so as to allow said operating table to be tilted;
   a display for displaying ultrasonic data obtained by the signal processing in said main body;
   a support member placed on said table for supporting said display, and rotating and tilting said display.

17. An apparatus according to claim 16, further comprising a rack portion pivotally attached to a shaft member, wherein said rack portion is fixedly attached at one end to a probe and at a second end to said shaft member.

* * * * *